United States Patent
Reszka et al.

(10) Patent No.: US 6,207,133 B1
(45) Date of Patent: Mar. 27, 2001

(54) ANTI-TUMORAL THERAPY AGENT CONTAINING A CONTRAST AGENT

(75) Inventors: Regina Reszka, Schwanebeck; Gerd Berger, Berlin; Uwe Pohlen, Berlin; Marion Jung, Berlin, all of (DE)

(73) Assignee: Max-Delbrück-Centrum für Molekulare Medizin (DE)

( * ) Notice: Subject to any disclaimer, the term of this patent is extended or adjusted under 35 U.S.C. 154(b) by 0 days.

(21) Appl. No.: 09/445,292
(22) PCT Filed: Jun. 4, 1998
(86) PCT No.: PCT/DE98/01514
  § 371 Date: Jun. 6, 2000
  § 102(e) Date: Jun. 6, 2000
(87) PCT Pub. No.: WO98/55103
  PCT Pub. Date: Dec. 10, 1998

(30) Foreign Application Priority Data

Jun. 6, 1997 (DE) ............................................. 197 24 796

(51) Int. Cl.$^7$ ........................... A61B 5/055; A61K 49/04; A61K 9/127
(52) U.S. Cl. ..................... 424/9.321; 424/9.4; 424/9.43; 424/9.45; 424/450
(58) Field of Search ................ 424/9.32, 9.321, 424/9.322, 9.35, 9.36, 9.364, 9.365, 9.4, 9.43, 9.45, 450, 489, 492, 493, 498, 499, 649; 600/420, 431

(56) References Cited

U.S. PATENT DOCUMENTS

| | | | |
|---|---|---|---|
| 4,590,060 | * | 5/1986 | Ehrenfeld .............................. 424/1.13 |
| 5,213,788 | * | 5/1993 | Ranney ................................ 424/9.322 |
| 5,213,804 | * | 5/1993 | Martin et al. ........................ 424/450 |
| 5,215,680 | * | 6/1993 | D'Arrigo .................................. 516/11 |
| 5,312,617 | * | 5/1994 | Unger et al. ........................ 424/9.365 |
| 5,387,410 | * | 2/1995 | Bosworth et al. ................. 424/9.321 |
| 5,512,294 | * | 4/1996 | Li et al. ................................ 424/450 |
| 5,582,172 | * | 12/1996 | Papisov et al. ...................... 600/431 |
| 5,620,703 | * | 4/1997 | Reszka et al. ....................... 424/450 |
| 5,705,187 | * | 1/1998 | Unger .................................. 424/450 |

FOREIGN PATENT DOCUMENTS 4341478     6/1995  (DE).
  98/44910  * 10/1998  (WO).

* cited by examiner

*Primary Examiner*—Gary E. Hollinden
(74) *Attorney, Agent, or Firm*—Norris, McLaughlin & Marcus P.A.

(57) ABSTRACT

The invention relates to a new anti-tumoral therapy agent based on liposome-encapsulated cytostatic agents and/or the metabolites thereof. The invention can be used in the pharmaceutical industry and in medicine. The aim of the invention is to build up drug targeting to combat cancer through suitable carrier systems. The invention is characterized by the fact that it clearly increases the concentration of cytostatic agents and residence time in tumors. At the same time, toxic side-effects on the remaining organs are reduced. The inventive agent contains PEG, immuno or immuno/PEG liposome-encapsulated cytostatic agents and/or the metabolites thereof, degradable starch particles and/or gelatin and/or nanoparticles, contrast agents containing iodine, gadolinium or magnetite. A preferred agent is characterized by the cytostatic agent Carboplatinum, encapsulated in SUV-PEG, starch particle Spherex or Gelfoam and the contrast agent Gadolinium-DTPA.

11 Claims, 13 Drawing Sheets

RESULTS

| TREATMENT FORM | TUMOR GROWTH BY THE FACTOR (7 DAYS AFTER THE TREATMENT) | ACCUMULATING OF CONTRASTING AGENT IN THE LIVER |
|---|---|---|
| CONTROL | 3.65 ± 2.45 | UNCHANGED |
| SPHEREX | 2.38 ± 1.35 | → 6% |
| GEL FOAM | 3.93 ± 1.66 | UNCHANGED |
| CARBOPLATIN | 1.45 ± 0.96 | → 7% |
| CARBOPLATIN/ SPHEREX | 1.15 ± 0.24 | → 19% |
| CARBOPLATIN/ GEL FOAM | 0.85 ± 0.08 | → 11% |

FIG. 1

CONCENTRATION AFTER LOCOREGIONAL APPLICATION
OF 50 ... CARBOPLATIN IN THE TUMOR/LIVER
ANIMAL EXPERIMENTAL STUDY OF VX-2 LIVER TUMOR OF RABBITS
WITHOUT EMBOLISATE, WITH 60 mg OF SPHEREX
AND WITH 10 mg OF GEL FOAM
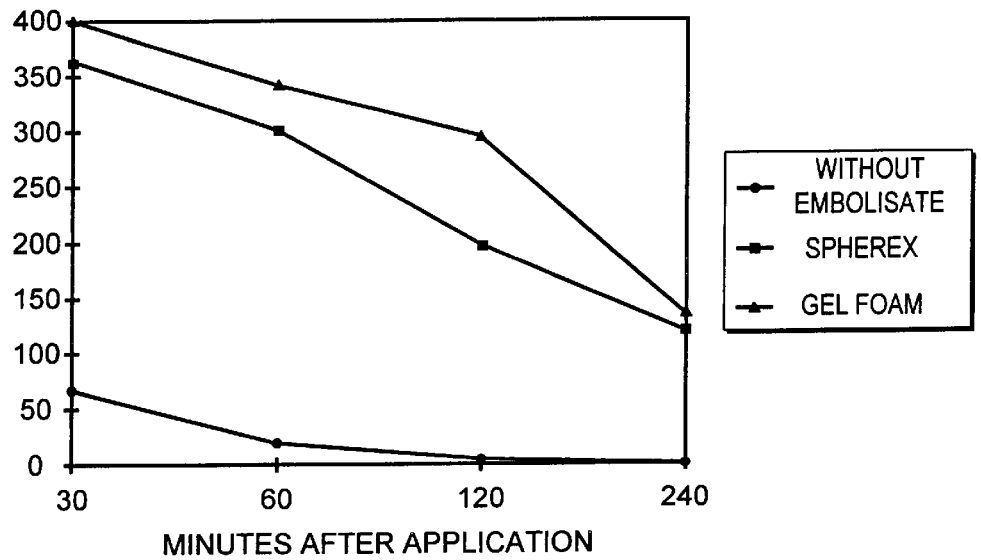
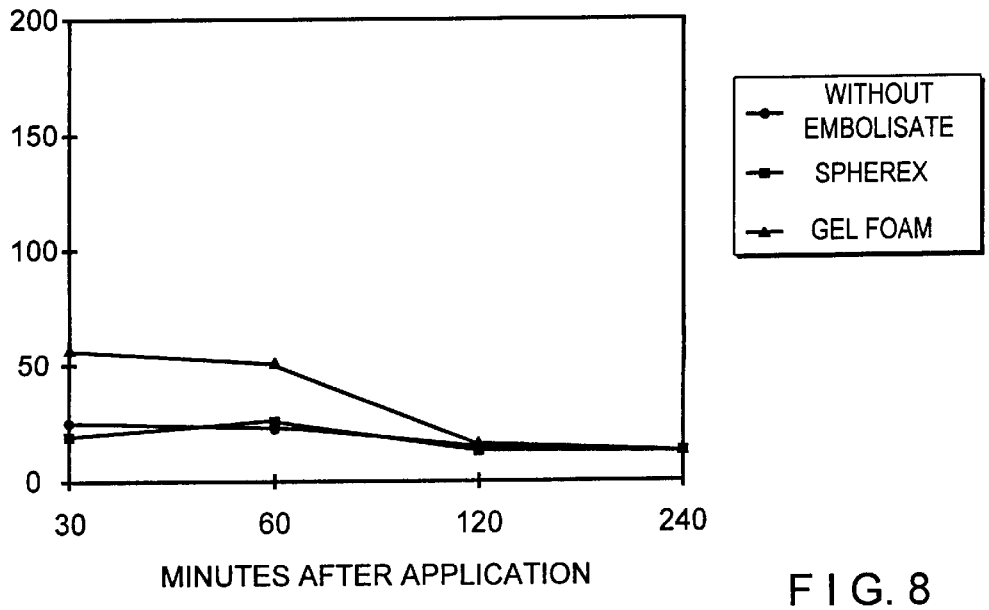
FIG. 8

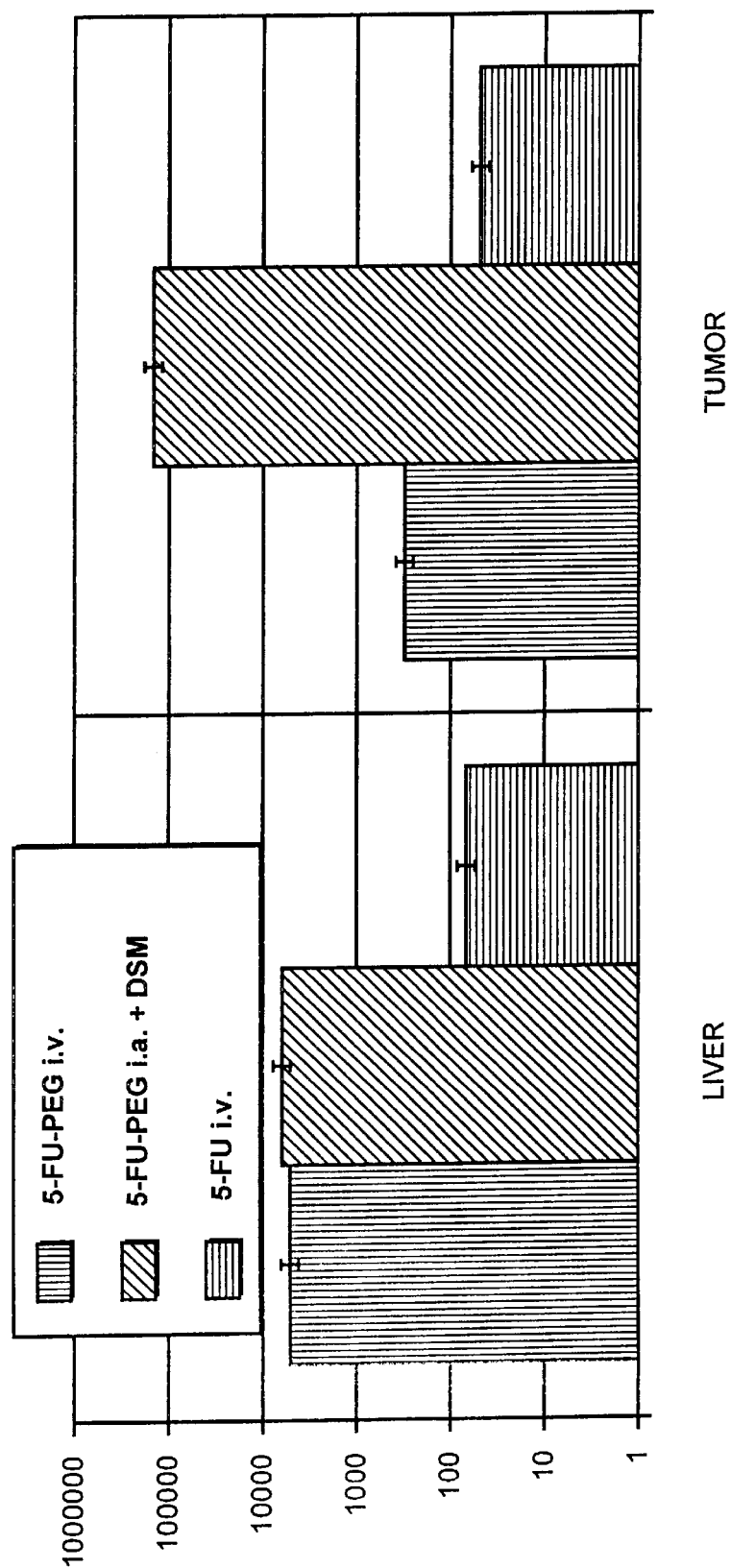

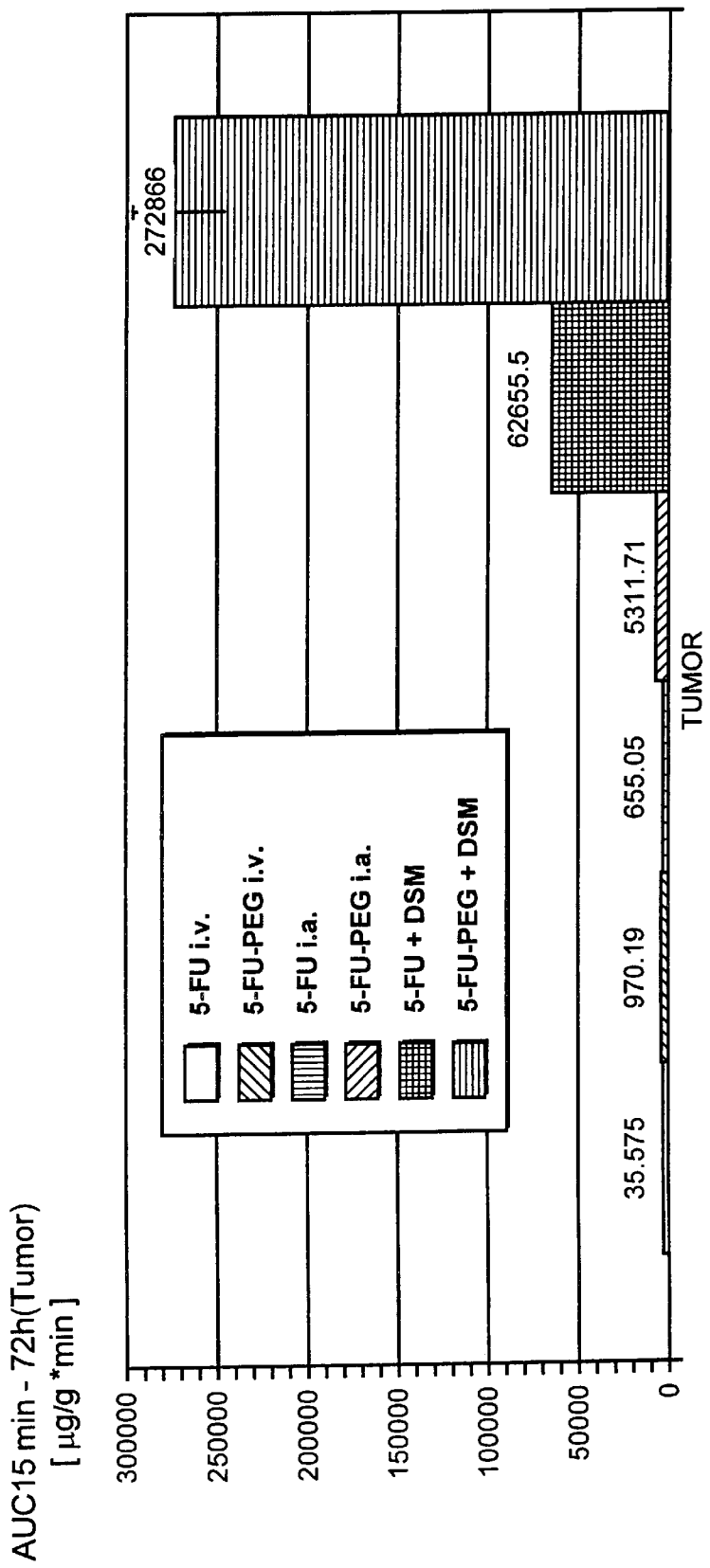

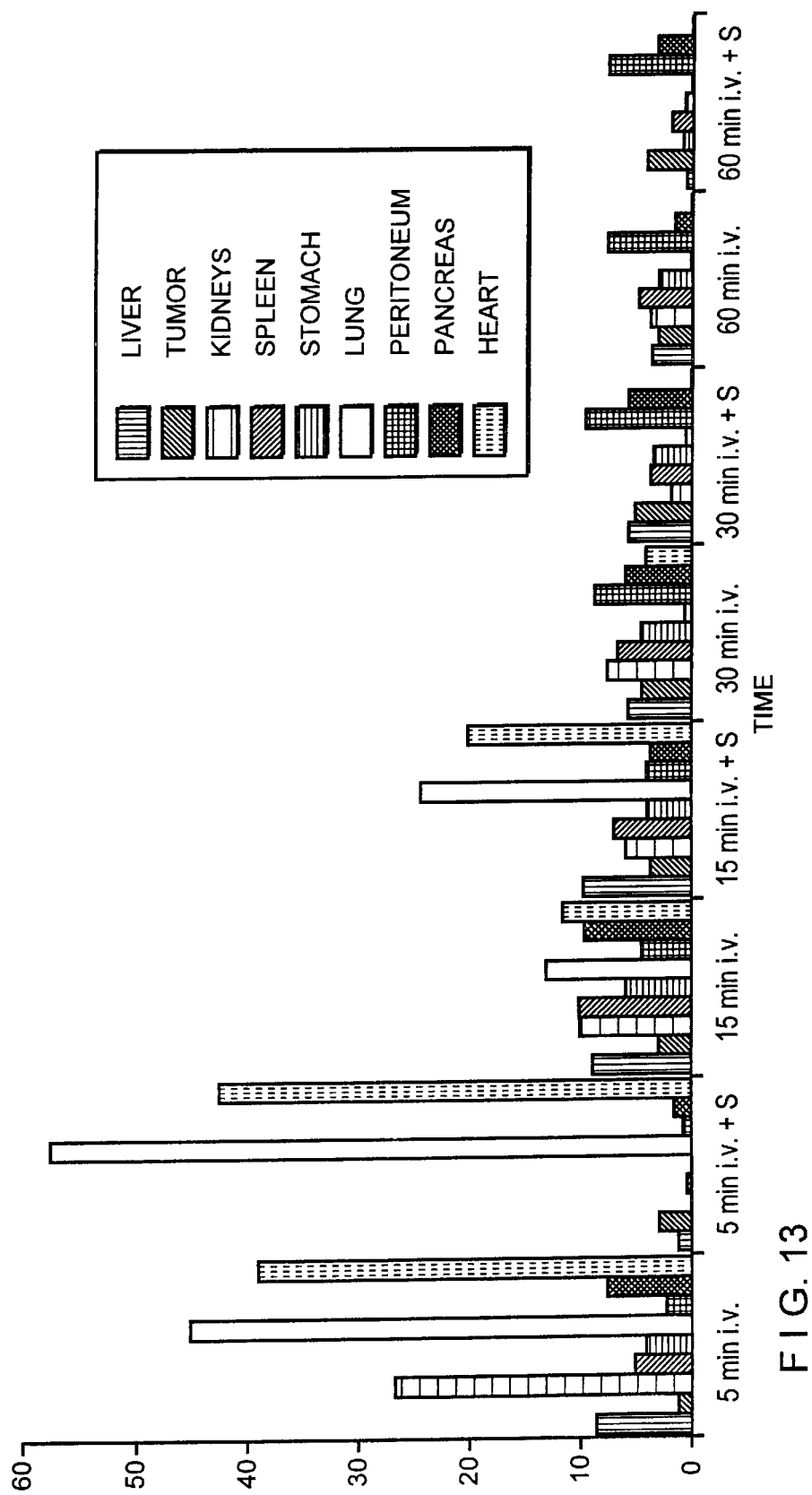

ANTI-TUMORAL THERAPY AGENT CONTAINING A CONTRAST AGENT

This application is a 371 of PCT/DE98/01514 Jun. 4, 1998.

BACKGROUND OF THE INVENTION

The invention relates to a new anti-tumoral therapy agent based on liposome-encapsulated cytostatic agents and/or the metabolites thereof. Fields of application of the invention are pharmaceutical industry and medicine.

A few agents for anti-tumoral therapy are known. In DE 43 41 478 an agent was described which, in particular, may be used for the therapy of non-resectable primary and secondary liver tumours. This agent contains lyophylized starch particles which are combined with one or a few cytostatic agents and dissolved in contrast agents containing iodine, gadolinium and magnetite. A preferred cytostatic agent for this agent is Carboplatin.

SUMMARY OF THE INVENTION

According to 43 41 478 by means of this agent a high concentration of the cytostatic agent used is reached in the tumour to be treated. However, a disadvantage consists in the fact that the residence time in the tumour totals only approx. 4–6 hours which, in general, is not sufficient for a successful therapy.

The aim of the invention is to build up drug targeting to combat cancer through suitable carrier systems. The invention is based on the task to increase distinctly the concentration of cytostatic agents and the residence time in tumours. At the same time, toxic side-effects on the remaining organs are to be reduced.

An essential aspect of the invention is the encapsulation of the cytostatic agents used and/or the metabolites thereof, preferably with PEG liposomes. Furthermore, the use of degradable starch particles resulting in retarding the flow and thus the contact time is of great importance.

The encapsulation of the cytostatic agents is implemented in a way known as such, e.g. by preparing a mixture of hydrogenated phosphatidylcholine, cholesterol, dicetyl phosphate and additionally polyethylene glycol in chloroform and diisopropyl ether.

Object of the invention are also the pharmaceutical preparations of the first component of the agent according to the invention consisting of a) natural, semisynthetic of fully synthetic amphipathic such as lipid, surface-active agent, emulsifier or polyethylene glycol (PEG) or lipid-PEG, b) a steroid, c) a charged lipid component, d) the cytostatic agent soluble in water or lipid and e) a carrier liquid and, if necessary, additional auxiliary agents such as e.g. nanoparticles.

The natural, semisynthetic or fully synthetic amphipathic has preferably the general formula I

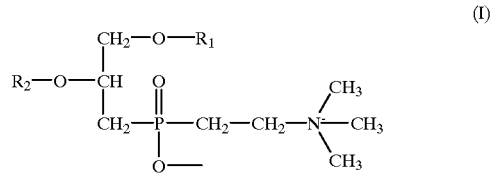

wherein $R_1$, and $R_2 = C_{10}$–C20-alcanoyl, alkenoyl, alkyl, alkenyl.

The steroid has preferably the general formula II

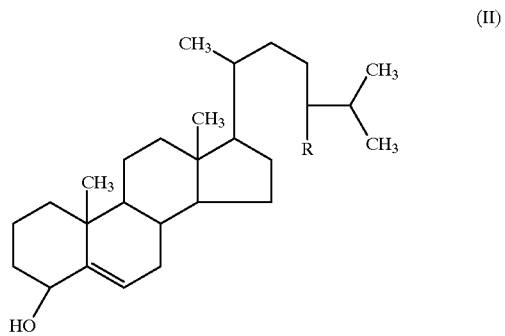

Wherein R=H (cholesterol) or $=CH_2$—$CH_2$—O—$CH_2$—OH (dicholesterol). The charged lipid component is preferably the anion of dicetyl phosphate, palmitic acid, stearic acid, the anion of a phospholipid such as phosphatidylserine, phosphatidic acid or the anion of a sphingolipid such as sulphatide or polyethylene glycol such as MPES-DSPE. Preferred cytostatic agents are Carboplatin, 5-fluorouracil and 5-fluorouridine. The quantity ratios of the components are preferably a:b:c in a molar ratio 1:0.3:0.1 up to 1:1:0.1 or up to 1:1:0.5 and c:d in a molar ration 2:1 up to 10:1.

The advantages of the new agent become visible in application. Compared to the known agents they consist in the essentially higher efficiency which is due to the fact that a higher quantity of the cytostatic agent may be brought into the tumour, staying there for a longer time. The so-called AUC value ("area under the curve"), the residence time and the quantity of the therapeutic agent collected in the tumour are decisive for the therapeutic effect. When applying the agent according to the instant invention this value is distinctly higher than in the case of the agents known, e.g. in the agent according to DE 43 41 478. FIG. 12 shows e.g. that the AUC of encapsulated 5-fluorouridine has been increased by 417 times as compared with the free compound (when adding degradable starch particles by 4.4 times).

The application regime of the agent according to the instant invention is also of importance. The intra-arterial application results mostly in a strong increase of the AUC. A further advantage essential for the practical application consists in the fact that the agent may be also applied orally.

The invention is explained in greater detail by examples of execution and the following FIGS. 1 to 13.

BRIEF DESCRIPTION OF THE DRAWINGS

Results with Carboplatin as cytostatic agent, encapsulation in SUV-PEG and Spherex or Gelfoam as starch particles FIG. 1 —comparison of the growth of tumors;

FIG. 8 is a graph showing the concentration after locoregional application of carboplatin.

Results with fluorouracil

Figure 2:
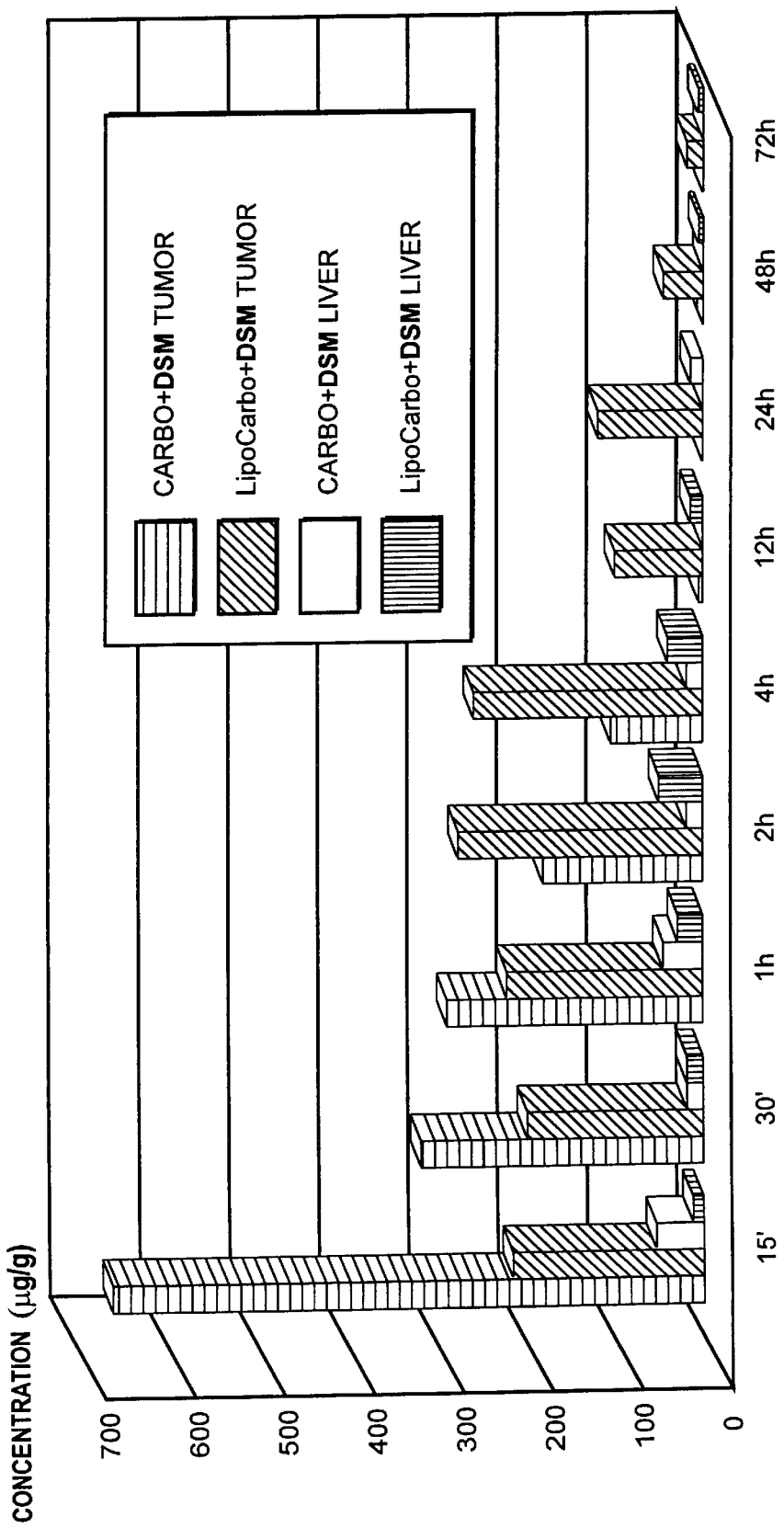
FIGS. 2–4—pharmakinetics in tumors and liver.
Figure 3:
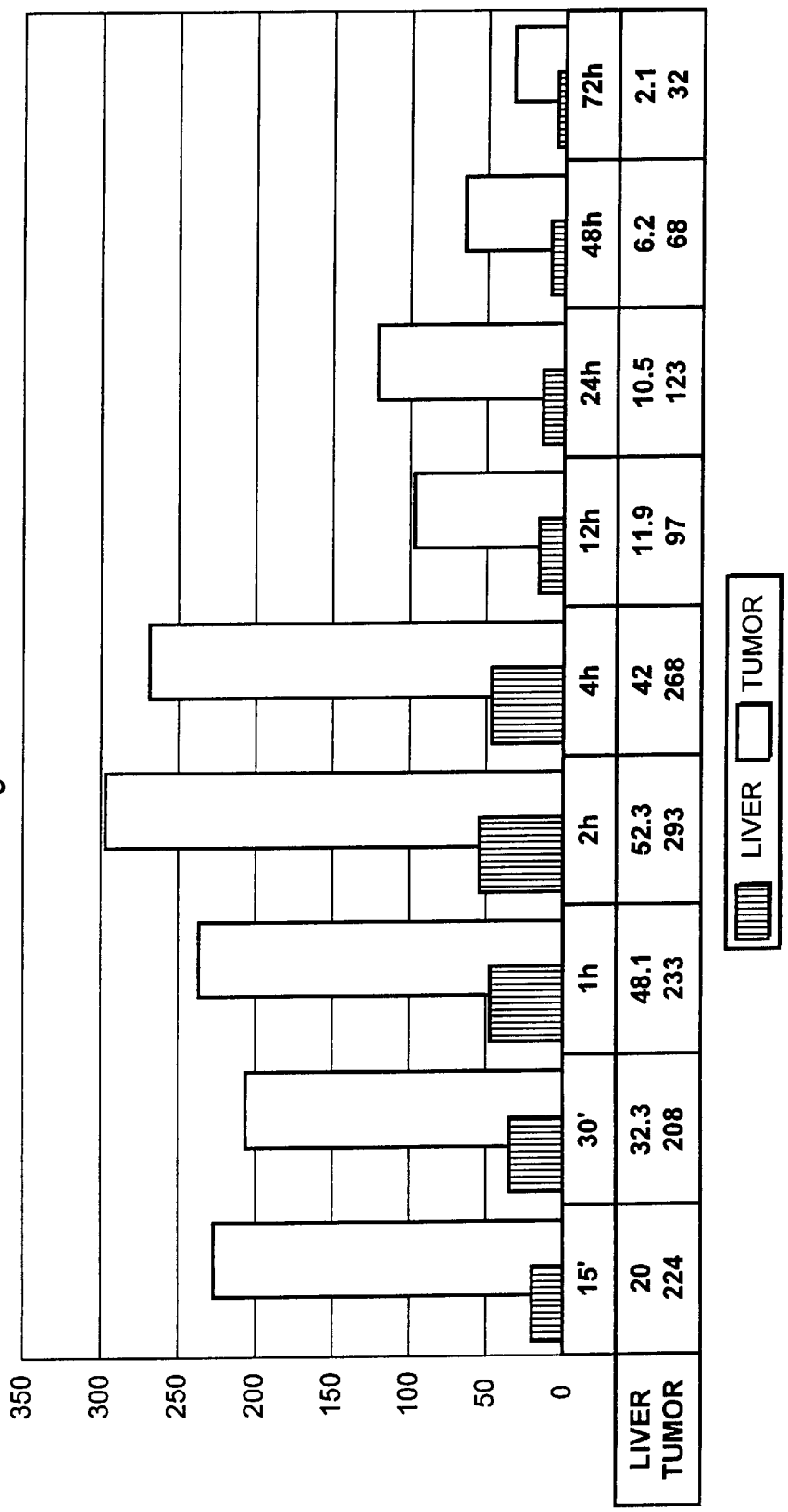
Figure 4:
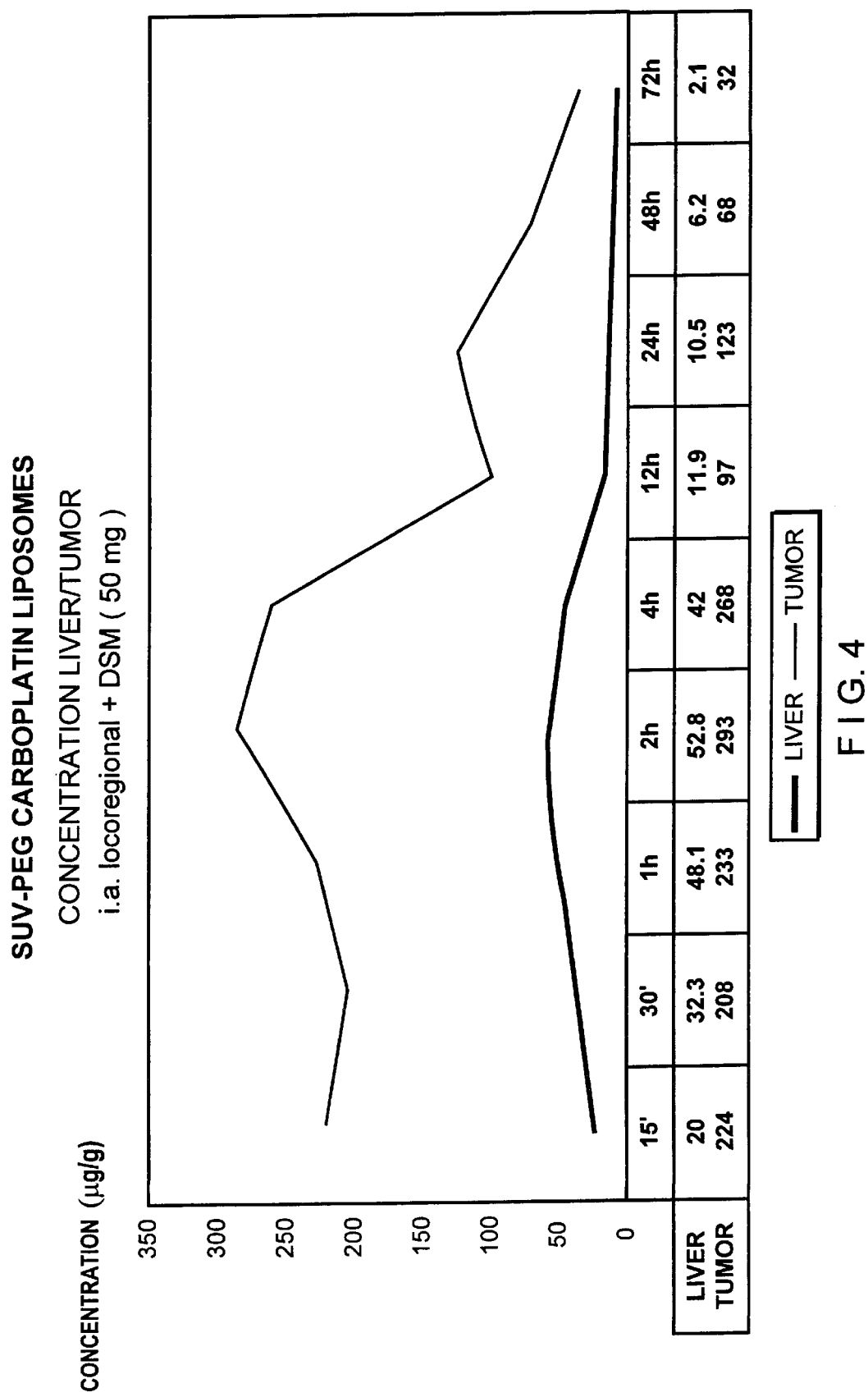
Figure 5:
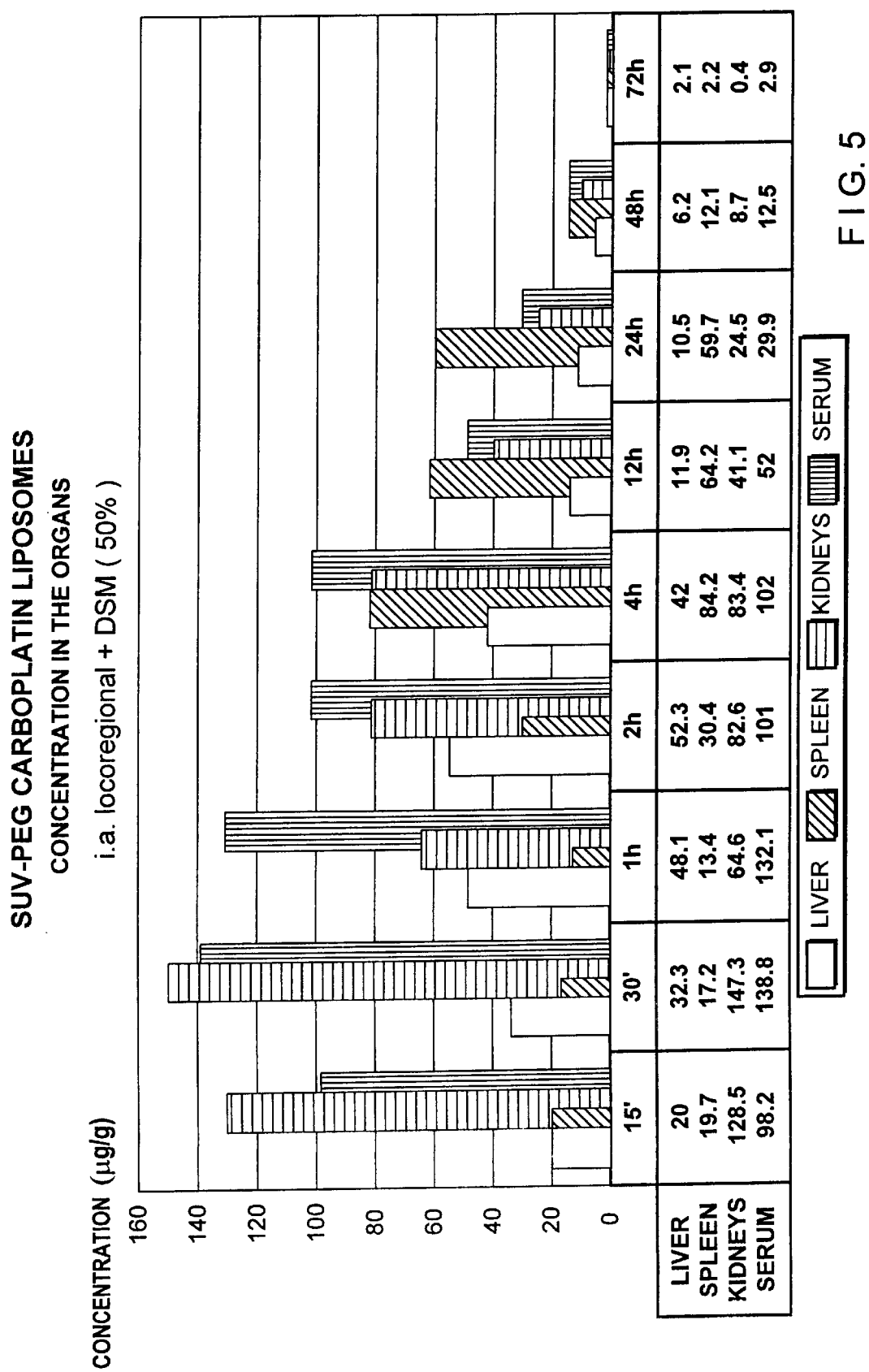
FIG. 5—concentration in the organs.
Figure 6:
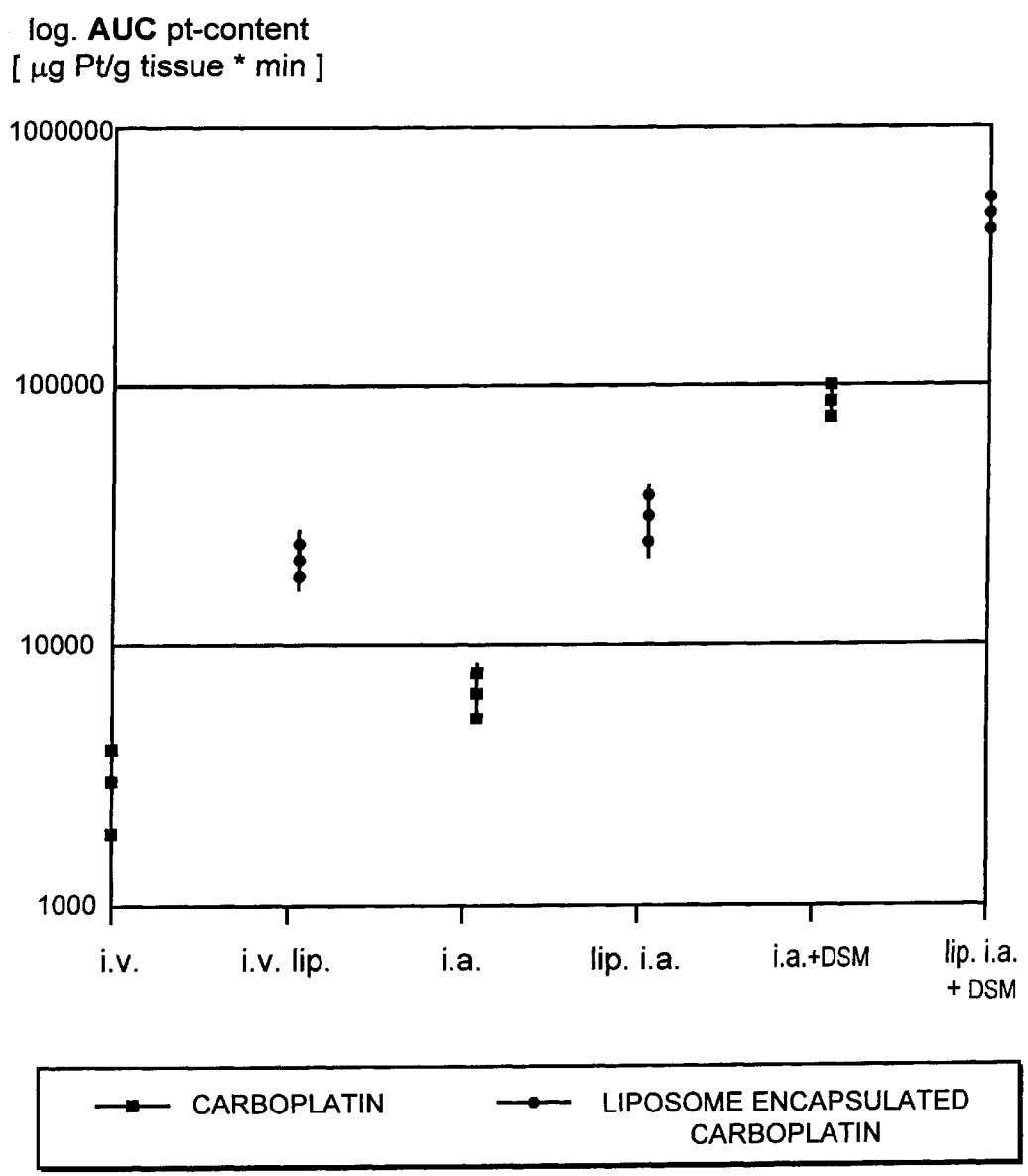
FIGS. 6–7—comparison of the areas below the Carboplatin/liposomal encapsulated Carboplatin curve.
Figure 7:
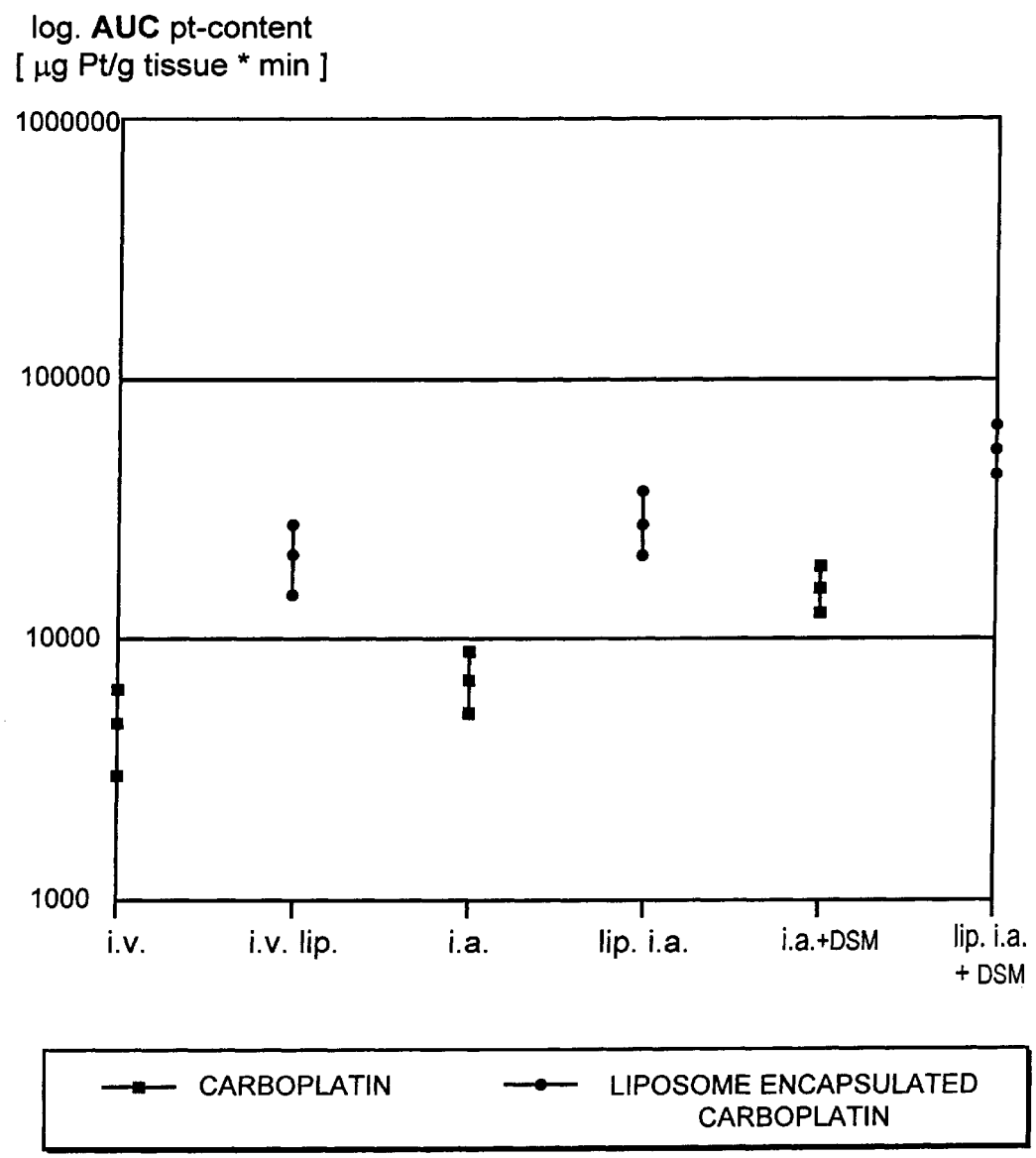
Figure 9:
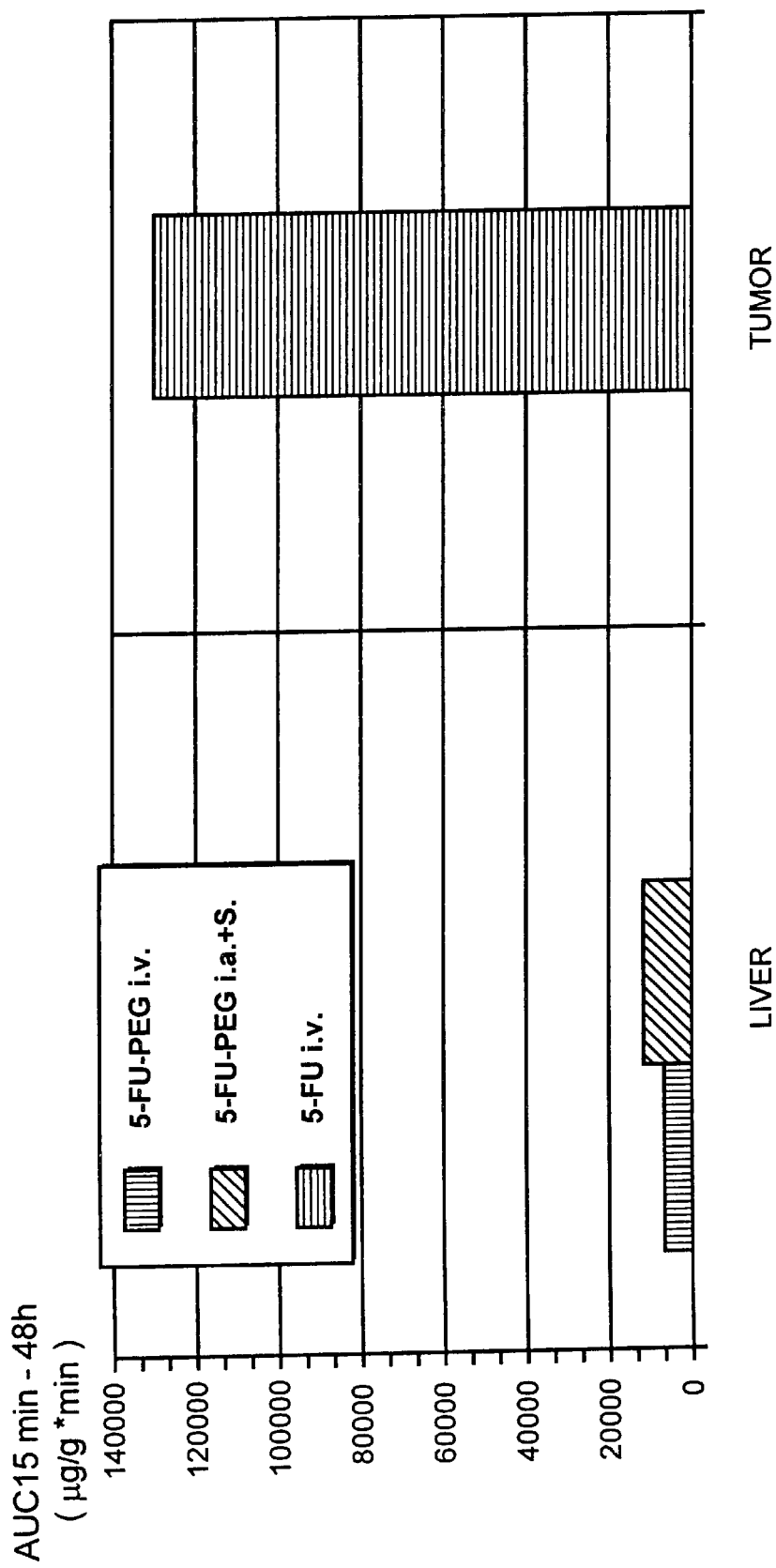
Figure 10:
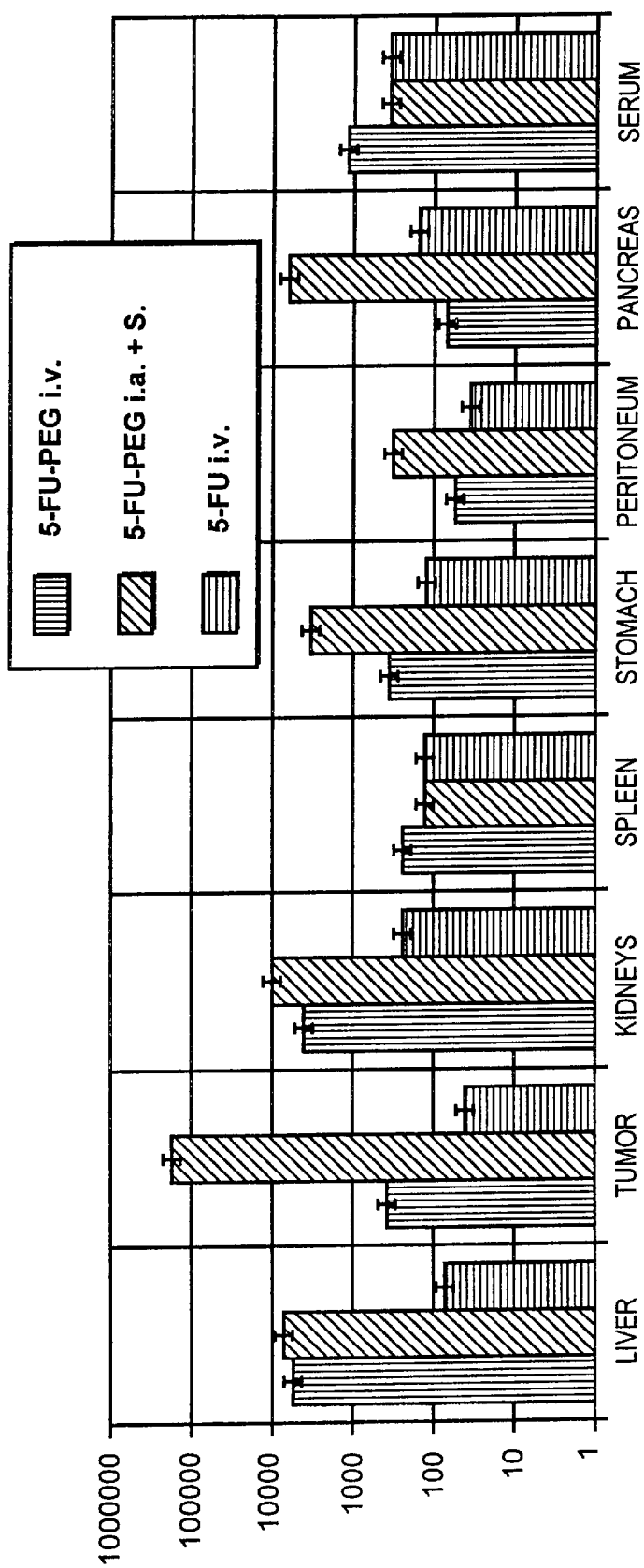

FIG. 9 —concentration in tumor and liver;

FIGS. 10–12—pharmakinetics and concentrations in various forms of application; and FIG. 13 —application with and without Spherex.

DESCRIPTION OF THE PREFERRED EMBODIMENT

Example 1

$1\times10^7$ vital VX2 tumour cells are implanted into the left lobe of the liver of male chinchilla rabbits.

After growth of a tumour of a size of 2 cm, following a fixed scheme, the animals were given either the therapeutic agent according to the instant invention or a mixture of the same doses of the commercially available form either as a hepatic artery infusion (HAI) through the port system or intravenously. It involves always 60 mg of degradable starch microspheres (Spherex), 50 mg of liposomal encapsulated Carboplatin and 5 ml of a 300 mg/ml contrast agent containing iodine (Ultravist 300, Schering). The animals were killed at fixed time points (15, 30, 60, 120, 240 min. 8 hours, 12 hours, 24 hours, 48 hours) and the concentration of the cytostatic agent in the tumour, liver, spleen, kidney, pancreas, stomach, lymph nodes was analytically detected, applying atomic absorption spectroscopy. The AUC for the liposomal Carboplatin was increased in the tumour by 20 times.

Example 2

The same procedure as in example 1. However, the CC 531 adenocarcinomas implanted into WAG/Ri j-rats were treated with the therapeutic agent according to the instant invention. In this model the animals were treated with 6 mg of Spherex, 10 mg of liposomal 5-FU and 0.5 ml of Ultravist. At the same time points, as described above, the animals were killed and the 5-FU concentration and the metabolite thereof were analytically detected applying HLPC. The AUC for the liposomal 5-FU in the tumour was increased by 20 times. The application of the newly developed agent could be observed directly by radiological checking without causing any problems, with the gradual saturation of the vascular bed of the tumour being demonstrated on standing pictures from the periphery to the vascular trunk throughout the phase of embolization and reconstructable as a standing picture during the whole period of vascular occlusion. It was equally possible to document the reperfusion setting in.

What is claimed is:

1. Anti-tumoral therapy agent based on liposome-encapsulated cytostatic agents and/or the metabolites thereof, comprising
   (a) one or both of cytostatic agents and the metabolites thereof encapsulated in one chosen from the group consisting of polyethylene glycol, immunoliposomes and immunopolyethlene glycol liposomes,
   (b) one or more chosen from the group consisting of degradable starch particles, and gelatin and nanoparticles,
   (c) contrast agent comprising one chosen from the group consisting of iodine, gadolinium and magnetite.

2. Agent according to claim 1 wherein the encapsulation of the cytostatic agents and/or the metabolites thereof is effected in one chosen from the group consisting of:
   small unilamelar vesicles-polyethylene glycol, large unilamellar vesicles-polyethylene glycol, reversed face evaporation vesicles-polyethylene glycol, and multilamellar vesicles-polyethylene glycol.

3. Agent according to claim 1 wherein the encapsulation of the cytostatic agents and/or the metabolites thereof is effected in
   anti-Ki-67-immun-PEG liposomes.

4. Agent according to claim 1 wherein the encapsulation of the cytostatic agents and/or the metabolites thereof is effected in
   anti-CEA-PEG liposomes.

5. Agent according to claim 1 wherein the starch particles have a particle size of 60–90 nm.

6. Agent according to claim 1 wherein the gelatin is absorbable gelatin powder.

7. Agent according to claim 1 wherein the nanoparticle is a 25% aqueous solution of Poloxamer.

8. Agent according to claim 1 wherein
   (a) the cytostatic agent is 5-fluorouracil, encapsulated in small unilamelar vesicles—polyethylene glycol;
   (b) the starch particle is Spherex; and
   (c) the contrast agent is Gadolinium-DTPA.

9. Agent according to claim 1 wherein
   (a) the cytostatic agent is 5-fluorouridin, encapsulated in small unilamelar vesicles—polyethylene glycol;
   (b) the starch particle is Spherex; and
   (c) the contrast agent is Gadolinium-DTPA.

10. Agent according to claim 1 wherein
    (a) the cytostatic agent is Carboplatin, encapsulated in small unilamelar vesicles—polyethylene glycol;
    (b) the starch particles are Spherex or Gelfoam; and
    (c) the contrast agent is Gadolinium-DTPA.

11. Agent according to claim 1 containing
    (a) the cytostatic agent is 5-fluorouridin-5'-hexadecylphosphate, encapsulated in small unilamelar vesicles-polyethylene glycol;
    (b) the starch particles are Spherex or Gelfoam; and
    (c) the contrast agent is Gadolinium-DTPA.

* * * * *